(12) United States Patent
Hotta

(10) Patent No.: US 11,795,145 B2
(45) Date of Patent: Oct. 24, 2023

(54) METHANE-PRODUCTION INHIBITOR COMPOSITION AND METHOD FOR INHIBITING METHANE PRODUCTION

(71) Applicant: KUMIAI CHEMICAL INDUSTRY CO., LTD., Tokyo (JP)

(72) Inventor: Yudai Hotta, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 17/919,080

(22) PCT Filed: Apr. 16, 2021

(86) PCT No.: PCT/JP2021/015740
§ 371 (c)(1),
(2) Date: Oct. 14, 2022

(87) PCT Pub. No.: WO2021/215365
PCT Pub. Date: Oct. 28, 2021

(65) Prior Publication Data
US 2023/0167053 A1 Jun. 1, 2023

(30) Foreign Application Priority Data
Apr. 21, 2020 (JP) ................ 2020-075593

(51) Int. Cl.
| C07C 317/14 | (2006.01) |
| C07C 309/66 | (2006.01) |
| C07C 317/22 | (2006.01) |
| C07C 309/65 | (2006.01) |
| C07C 309/68 | (2006.01) |
| A23K 50/10 | (2016.01) |
| A23K 20/111 | (2016.01) |
| C09K 17/14 | (2006.01) |

(52) U.S. Cl.
CPC .......... *C07C 317/14* (2013.01); *A23K 20/111* (2016.05); *A23K 50/10* (2016.05); *C07C 309/65* (2013.01); *C07C 309/66* (2013.01); *C07C 309/68* (2013.01); *C07C 317/22* (2013.01); *C09K 17/14* (2013.01); *Y02E 50/30* (2013.01)

(58) Field of Classification Search
CPC ... C07C 317/14; C07C 309/66; C07C 317/22; C07C 309/65; C07C 309/68; A23K 20/111; A23K 50/10; Y02E 50/30; C09K 17/14
See application file for complete search history.

(56) References Cited

U.S. PATENT DOCUMENTS

| 3,608,087 A | 9/1971 | Patchett |
| 4,013,794 A | 3/1977 | Maurer et al. |
| 2003/0008895 A1 | 1/2003 | Cameron et al. |
| 2003/0219467 A1 | 11/2003 | Miner et al. |
| 2010/0137136 A1 | 6/2010 | Rosinger et al. |
| 2010/0285959 A1 | 11/2010 | Armel et al. |
| 2014/0147529 A1 | 5/2014 | Duval et al. |
| 2015/0376113 A1 | 12/2015 | Duval et al. |

FOREIGN PATENT DOCUMENTS

| CN | 101611762 | 12/2009 |
| CN | 102223795 | 10/2011 |
| JP | 50-15710 | 6/1975 |
| JP | 63-104903 | 5/1988 |
| JP | 63-112554 | 5/1988 |
| JP | 2002-281912 | 10/2002 |
| WO | 2012/084629 | 6/2012 |

OTHER PUBLICATIONS

Shiraishi et al. ( "Identification and Determination of 4-(Chloromethylsulfonyl)bromobenzene, A New Herbicide Additive, In Lake Waters", Water Research, vol. 21, No. 7, 1987, pp. 843-847). (Year: 1987).*
Jain et al. ( "Studies in Sulphones. Part III* Synthesis of New Contact Insecticides", Journal of The Indian Chemical Society, vol. XXIV, 1947, pp. 220-222). (Year: 1947).*
International Search Report (ISR) dated Jul. 13, 2021 in International (PCT) Application No. PCT/JP2021/015740.

(Continued)

*Primary Examiner* — Rosalynd A Keys
(74) *Attorney, Agent, or Firm* — Wenderoth, Lind & Ponack, L.L.P.

(57) ABSTRACT

Provided are a methane-production inhibitor capable of inhibiting methane production for a long period of time, and a method for inhibiting methane production using the composition. A methane-production inhibitor composition contains one or more compounds selected from compounds represented by formula [I] as an effective ingredient, and a method for inhibiting methane production uses the composition.

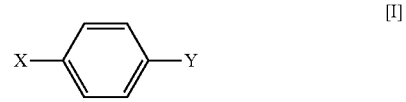

[I]

(In formula [I], X represents an —OR$_1$ group, a hydroxyl group, or a halogen atom, Y represents an —OR$_2$ group or an —SO$_2$R$_3$ group, R$_1$ represents a benzoyl group, R$_2$ represents a methylsulfonyl group or a chloromethylsulfonyl group, and R$_3$ represents a chloromethyl group or a hydroxymethyl group.)

10 Claims, No Drawings

(56) References Cited

OTHER PUBLICATIONS

Tatoba R. Waghmode et al., "Effective Suppression of Methane Emission by 2-Bromoethanesulfonate during Rice Cultivation", PLOS One, 10(11): e0142569, pp. 1-13, Nov. 12, 2015, cited in the specification.

Alexander N. Hristov et al., "An inhibitor persistently decreased enteric methane emission from dairy cows with no negative effect on milk production", PNAS, vol. 112, No. 34, pp. 10663-10668, Aug. 25, 2015, cited in the specification.

* cited by examiner

METHANE-PRODUCTION INHIBITOR COMPOSITION AND METHOD FOR INHIBITING METHANE PRODUCTION

TECHNICAL FIELD

The present invention relates to a methane-production inhibitor composition and a method for inhibiting methane production. In particular, the present invention relates to a methane-production inhibitor composition capable of inhibiting methane production for a long period of time, and a method for inhibiting methane production using the composition.

BACKGROUND ART

Methane is the second largest greenhouse gas after carbon dioxide, and the annual contribution of methane to global warming is reported to be about 40%. Major sources of methane production are paddy fields, ruminants, and natural wetlands, with estimated methane emissions from paddy field soils accounting for from 5 to 19% of total emissions. As methods for reducing methane emissions in paddy fields, limiting the period of soil immersion (midsummer drainage) and reducing carbon inputs have been proposed. As another method for methane reduction, a method of treating paddy fields with 2-bromoethanesulfonate (BES, 80 mg/kg), a specific inhibitor of methane-producing bacteria, during rice cultivation has been proposed, by which methane emissions were reduced by 49% compared to a control area (see Non-patent Document 1).

In the livestock industry, methane emissions from dairy cattle have been reduced by 30% by treating feed with from 40 to 80 mg/kg of 3-nitrooxypropanol (3-NOP), a methane-production inhibitor (see Patent Document 1, Non-patent Document 2).

RELATED ART DOCUMENTS

Patent Document

[Patent Document 1] WO 2012/84629

Non-Patent Documents

[Non-patent Document 1] Waghmode T R et. al. (2015) PLoS ONE 10(11): e0142569
[Non-patent Document 2] Hristov A N et. al. (2015) Proc. Natl. Acad. Sci. USA, 112, 10663-10668

SUMMARY OF THE INVENTION

Problems to be Solved by the Invention

However, no previously known methane-production inhibitors have been put to practical use, and even today, development and practical application of superior methane-production inhibitors are still desired. The present invention has been made in view of such problems, and a principal object of the present invention is to provide a methane-production inhibitor composition having a sustained methane-production inhibiting effect at a low amount of chemicals and a method for inhibiting methane production, in order to reduce undesirable methane production in paddy fields, lakes, marshes, and the like.

Means for Solving the Problems

Specifically, in order to achieve the above-described objectives, the present inventor diligently conducted studies to find that application of a specific compound to places where methane is generated and to livestock feed reduces the amount of methane produced and maintains the effect, thereby completing the present invention.

The present invention, completed as described above, has the following gist.

(1) A methane-production inhibitor composition, characterized by containing one or more compounds selected from compounds represented by formula [I] as an effective ingredient:

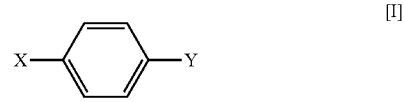

[I]

where X represents an —$OR_1$ group, a hydroxyl group, or a halogen atom, Y represents an —$OR_2$ group or an —$SO_2R_3$ group, $R_1$ represents a benzoyl group, $R_2$ represents a methylsulfonyl group or a chloromethylsulfonyl group, and $R_3$ represents a chloromethyl group or a hydroxymethyl group.

(2) The methane-production inhibitor composition according to the above-described (1), wherein the compound represented by formula [I] is any one of compounds represented by formulas [I-1] to [I-6].

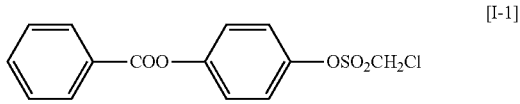

[I-1]

[I-2]

[I-3]

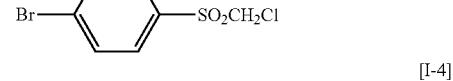

[I-4]

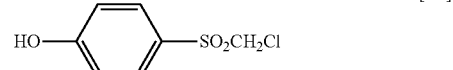

[I-5]

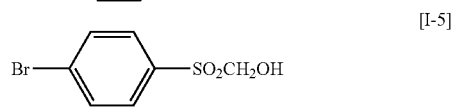

[I-6]

(3) A method for inhibiting methane production characterized in that the methane-production inhibitor composition according to the above-described (1) or (2) is applied to a water system or soil in which methane is generated thereby inhibiting methane production from the water system or soil.
(4) The method for inhibiting methane production according to the above-described (3), wherein the water system in which methane is generated is a paddy field or a lake or marsh.
(5) The method for inhibiting methane production according to the above-described (3), wherein the soil in which methane is generated is peatland.

(6) The method for inhibiting methane production according to any one of the above-described (3) to (5), wherein the amount of methane-production inhibitor composition applied is an amount in the range of from 50 to 5,000,000 g of the compound represented by formula [I] per 1 ha of area of the water system or soil in which methane is generated.

(7) A method for inhibiting methane production characterized in that the methane-production inhibitor composition according to the above-described (1) or (2) is mixed with feed and fed to livestock thereby inhibiting methane production from livestock breath and excreta.

(8) The method for inhibiting methane production according to the above-described (7), wherein the amount of methane-production inhibitor composition used is an amount in the range of from 0.05 to 5,000 mg of the compound represented by formula [I] per 1 kg of the feed.

(9) A method for inhibiting methane production characterized in that the methane-production inhibitor composition according to the above-described (1) or (2) is mixed with a compost or leaf mold material and fermented, thereby inhibiting methane production from a fermentation process of compost or leaf mold and from fully ripe compost or fully ripe leaf mold.

(10) The method for inhibiting methane production according to the above-described (9), wherein the amount of the methane-production inhibitor composition used is an amount in the range of from 0.05 to 5,000 mg of the compound represented by formula [I] per 1 kg of the compost or leaf mold material.

Effects of the Invention

The methane-production inhibitor composition of the present invention can inhibit methane generation from a paddy field and a lake or marsh, a livestock production site, a compost or humus production site, a peatland, or the like for a long period of time, and in turn, is a useful invention as a measure to prevent global warming.

MODE FOR CARRYING OUT THE INVENTION

The methane-production inhibitor composition of the present invention contains one or more compounds selected from compounds represented by formula [I] as an effective ingredient:

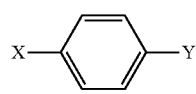

where X represents an —$OR_1$ group, a hydroxyl group, or a halogen atom, Y represents an —$OR_2$ group or an —$SO_2R_3$ group, $R_1$ represents a benzoyl group, $R_2$ represents a methylsulfonyl group or a chloromethylsulfonyl group, and $R_3$ represents a chloromethyl group or a hydroxymethyl group.

Suitable examples of the compounds represented by formula [I] include compounds represented by formulas [I-1] to [I-6].

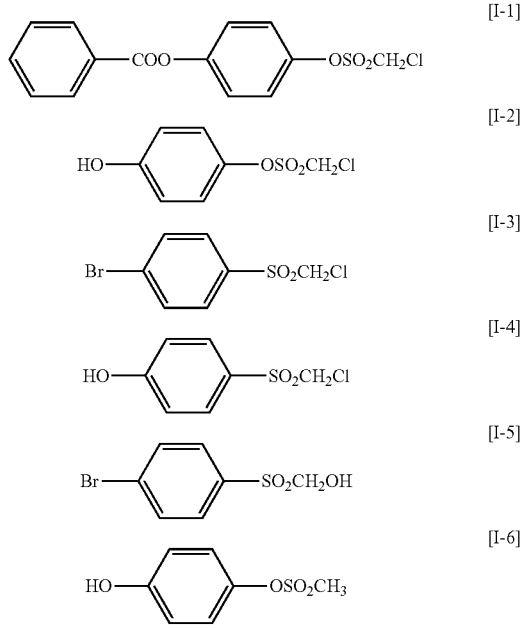

The compound of formula [I-1] (hereinafter, referred to as "Compound I-1") is a compound known by the CAS number of 117224-50-7 and can be synthesized by the method described in JP S63-112554A. The compound of formula [I-2] (hereinafter, referred to as "Compound I-2") is a compound known by the CAS number of 117224-69-8, and can be purchased from Chemieliva Pharmaceutical Co., Ltd. The compound of formula [I-3] (hereinafter, referred to as "Compound I-3") is a compound known by the CAS number of 54091-06-4 and can be purchased from Sigma-Aldrich. The compound of formula [I-4] (hereinafter, referred to as "Compound I-4") is a compound known by the CAS number of 56773-30-9 and can be purchased from Sigma-Aldrich. The compound of formula [I-5] (hereinafter, referred to as "Compound I-5") is a compound known by the CAS number of 872793-78-7 and can be purchased from Azepine Ltd. The compound of formula [I-6] (hereinafter, referred to as "Compound I-6") is a compound known by the CAS number of 59722-33-7 and can be purchased from Chemieliva Pharmaceutical Co. Ltd.

The methane-production inhibitor composition of the present invention may be the compound represented by formula [I] by itself or may contain an additive component if necessary. Examples of such an additive component include a carrier such as a solid carrier or a liquid carrier, a surfactant, a binder, an adhesive agent, a thickener, a coloring agent, a spreading agent, a spreading agent, an anti-freezing agent, an anti-caking agent, a disintegrant, an anti-degradation agent, and a polymeric material.

The methane-production inhibitor composition of the present invention may be used in any formulation, such as a liquid formulation, an emulsion concentrate, a wettable powder, a water-dispersible granule, a dust, an oil formulation, a flowable formulation, a granule formulation, a tablet formulation, a jumbo formulation, a suspoemulsion, a microcapsule, a paste, a seed coating formulation, a fumigant formulation, a smoking formulation, a Mametsubu (registered trademark name) formulation, a gelling formulation, a spraying formulation, a vulcanizing formulation, or a sheet formulation. These formulations can be prepared in the fields of pharmaceuticals, agrochemicals, or foods using the above-described additive components commonly used in formulation, using commonly known methods.

Since the methane-production inhibitor composition of the present invention can inhibit methane production for a long period of time, the composition can be used at a variety of places where methane is generated such as a water system such as a paddy field and a lake or marsh, a peatland, a livestock production site, and a compost or humus production site, and is useful as a measure to prevent global warming, and is especially suitable for use in a place where methane production is high, for example, in paddy fields.

In the method for inhibiting methane production of the present invention, the methane-production inhibitor composition of the present invention is applied to a water system where methane is generated, such as a paddy field or a lake or marsh, or to soil where methane is generated such as a peatland, thereby inhibiting methane production from the water system or the soil. Here, the lake or marsh is broadly defined as a body of water with shallow depth, such as a lake, a pond, a swamp, a stream, or a lagoon, for example, with a depth of 1 m or less. The soil where methane is generated such as a peatland broadly refers to soil where methane is generated due to the presence of organic matter in a reduced state, such as a wetland soil, a swamp soil, or a paddy field soil.

The method for applying the methane-production inhibitor composition of the present invention to a water system is not particularly limited, and it is sufficient to apply the compound represented by formula [I] in such a manner that the compound is dissolved or dispersed throughout the water system in which methane generation is to be inhibited, and this may be carried out using a commonly used application method, namely, a method such as spraying or pouring the methane-production inhibitor composition of the present invention as it is, or as a liquid suspended in a solvent such as water or acetone, throughout a water system.

The method for applying the methane-production inhibitor composition of the present invention to methane-producing soil such as a peatland is not particularly limited, and the entire surface of the soil can be sprayed with the methane-production inhibitor composition of the present invention. It is preferable that the surface soil of the soil is mixed after the application, allowing the methane-production inhibitor composition of the present invention to be mixed into the soil.

When the methane-production inhibitor composition of the present invention is applied to a water system, such as a paddy field and a lake or marsh, or a peatland, the amount of the compound represented by formula [I] per 1 kg of dry soil is desirably in the range of from 0.05 to 5,000 mg, preferably from 0.1 to 1,000 mg, more preferably from 0.5 to 500 mg, and most preferably from 0.5 to 100 mg. The methane-production inhibitor composition of the present invention applied in such a manner can effectively inhibit methane production when present in the surface soil to a depth of 10 cm.

When the above-described application amount is expressed in terms of an amount to be applied per 1 ha of area of a water system or soil to be applied, for example, in cases where the dry specific gravity (provisional specific gravity) of the soil is 1.0, application of the compound represented by formula [I] in an amount in the range of from 50 to 5,000,000 g, preferably from 100 to 1,000,000 g, more preferably from 500 to 500,000 g, and most preferably from 500 to 100,000 g corresponds to the amount applied per dry soil as described above. However, it is known that the dry specific gravity (provisional specific gravity) of soil varies depending on the soil type, and for example, the dry specific gravity is about from 1.1 to 1.8 for sandy soils, from 0.5 to 0.8 for black granite soils, and from 0.2 to 0.6 for peat soils. When the dry specific gravity (provisional specific gravity) of soil at a location to be applied is considerably different from 1.0, the above-described application amount per 1 ha of area may be multiplied by the value of the dry specific gravity (provisional specific gravity) of the soil.

In a water system such as a paddy field or a lake or marsh, the methane-production inhibitor composition of the present invention can be applied to the surface of the water, and the compound represented by formula [I] is distributed mostly to the surface layer of soil in contact with the water, after which methane production from the soil will be inhibited. In this case, the depth of the water system is desirably not too deep, and in a lake or marsh, the water depth is preferably 1 m or less, and more preferably 50 cm or less. Although, in paddy fields, the water depth is usually about from 3 to 5 cm, the composition can also be used in paddy fields managed with water depths as deep as 15 cm. When the methane-production inhibitor composition of the present invention is applied to the surface of a paddy field or lake or marsh, the concentration of the compound represented by formula [I] in water may be, for example, from 0.05 to 5,000 ppm, and preferably from 0.1 to 1,000 ppm, more preferably from 0.5 to 500 ppm, and most preferably from 0.5 to 100 ppm. The amount of the methane-production inhibitor composition of the present invention applied can also be calculated by the total water volume estimated from the area and water depth of a paddy field or a lake or marsh, such that the concentration of the compound represented by formula [I] in water is within the above-described range.

In the method for inhibiting methane production of the present invention, the methane-production inhibitor composition of the present invention can also be mixed with livestock feed and fed to livestock to inhibit methane generation from livestock breath and excreta. The method for mixing the methane-production inhibitor composition of the present invention with feed is not particularly limited, and the methane-production inhibitor composition of the present invention may be mixed with feed prior to feeding to livestock. In this case, the amount of the methane-production inhibitor composition of the present invention to be applied may be determined by calculating the amount of the compound represented by formula [I] per 1 kg of feed to be in the range of from 0.05 to 5,000 mg, preferably from 0.1 to 1,000 mg, further preferably from 0.5 to 500 mg, and most preferably from 0.5 to 100 mg.

Furthermore, in the method for inhibiting methane production, the methane-production inhibitor composition of the present invention can be applied to a compost or leaf mold material during production of the compost or leaf mold, thereby inhibiting generation of methane during production of the compost or leaf mold and from the produced compost or leaf mold. The method for applying the methane-production inhibitor composition of the present invention for this purpose is not particularly limited, and the methane-production inhibitor composition of the present invention can be mixed with a compost or leaf mold material and fermented to inhibit methane produced in a fermentation process of compost or leaf mold or methane produced from fully ripe compost or fully ripe leaf mold. In this case, the amount of methane-production inhibitor composition of the present invention to be applied may be calculated such that the amount of the compound represented by formula [I] per 1 kg of a compost or leaf mold material is in the range of from 0.05 to 5,000 mg, preferably from 0.1 to 1,000 mg, more preferably from 0.5 to 500 mg, and most preferably from 0.5 to 100 mg.

EXAMPLES

Hereinafter, an effect of the methane-production inhibitor of the present invention will be described with Test Examples, but the present invention is not restricted by these Test Examples in any way.

[Test Example 1] Methane-Production Inhibition Test by Methane-Production Inhibitor (Compound I-1)

In a glass vial (21.5 mL volume) for headspace analysis, 4.0 g of paddy field soil (provisional specific gravity 1.18 g/cm$^3$) was weighed, and 8 mL of distilled water was added. In this flooded soil, a plot to which 40 µL of 10 ppm Compound I-1-containing acetone solution was added (0.1 mg/kg dry soil (equivalent to 118 g/ha)) was provided as Example 1, and a plot to which 20 µL of 100 ppm Compound I-1-containing acetone solution was added (0.5 mg/kg dry soil (equivalent to 590 g/ha)) and a plot to which 40 µL of 100 ppm Compound I-1-containing acetone solution was added (1 mg/kg dry soil (equivalent to 1180 g/ha)) were provided as Examples 2 and 3. As Comparative Example 1, an untreated plot to which 40 µL of acetone was added was provided. After 100 µL of a culture solution of paddy field soil microorganisms was added to these glass vials, the vials were tightly sealed using septum and aluminum caps, and allowed to stand at 30° C. for static incubation. After 21 and 28 days of incubation treatment, 0.5 mL of gas was collected from a headspace in a glass vial sample using a gas tight syringe and analyzed for methane production by gas chromatography (GC). The results are shown in Table 1. The amount treatment (g) per 1 ha was converted according to the OECD Guideline Test No. 307 issued in 2002, based on the provisional specific gravity of the paddy field soil used.

TABLE 1

| | Compound | Treatment amount (mg/kg dry soil) | Methane-production amount (mg/L) | |
|---|---|---|---|---|
| | | | 21 days after treatment | 28 days after treatment |
| Example 1 | Compound I-1 | 0.1 | 9.1 | 21.3 |
| Example 2 | Compound I-1 | 0.5 | 2.8 | 3.7 |
| Example 3 | Compound I-1 | 1 | 2.5 | 3.1 |
| Comparative Example 1 | Untreated | — | 34.0 | 38.9 |

In Test Example 1, compared to an untreated plot (Comparative Example 1), the methane-production amount was reduced in the Compound I-1 treatment plot (Example 1) at 0.1 mg/kg dry soil, and a higher reduction effect was achieved at 0.5 mg/kg dry soil and above (Examples 2 and 3).

[Test Example 2] Methane-Production Inhibition Test by Various Methane-Production Inhibitor In a glass vial (21.5 mL volume) for headspace analysis, 4.0 g of paddy field soil (provisional specific gravity 1.18 g/cm$^3$) was weighed, and 8 mL of distilled water was added. In this flooded soil, plots to which 40 µL of acetone solution containing 50 ppm of the compounds listed in Table 2 below were added (0.5 mg/kg dry soil (equivalent to 590 g/ha)), respectively, were provided as Examples 4 to 9. As Comparative Example 2, an untreated plot to which 40 µL of acetone was added was provided. After 100 µL of a culture solution of paddy field soil microorganisms was added to these glass vials, the vials were tightly sealed using septum and aluminum caps, and allowed to stand at 30° C. for static incubation. After 21 and 28 days of incubation treatment, 0.5 mL of gas was collected from a headspace in a glass vial sample using a gas tight syringe and analyzed for methane production by gas chromatography (GC). The results are shown in Table 2.

TABLE 2

| | Compound | Treatment amount (mg/kg dry soil) | Methane-production amount (mg/L) | |
|---|---|---|---|---|
| | | | 21 days after treatment | 28 days after treatment |
| Example 4 | Compound I-1 | 0.5 | 2.5 | 3.8 |
| Example 5 | Compound I-2 | 0.5 | 2.5 | 4.4 |
| Example 6 | Compound I-3 | 0.5 | 5.3 | 14.7 |
| Example 7 | Compound I-4 | 0.5 | 5.4 | 16.7 |
| Example 8 | Compound I-5 | 0.5 | 15.7 | 24.3 |
| Example 9 | Compound I-6 | 0.5 | 16.7 | 28.3 |
| Comparative Example 2 | Untreated | — | 19.6 | 44.3 |

In Test Example 2, the methane-production amount was reduced in all of the various methane-production inhibitor treatment plots (Examples 4 to 9) compared to the untreated plot (Comparative Example 2). In the 0.5 mg/kg dry soil treatment, Compound I-1 and Compound 1-2 showed a particularly high reduction effect (Examples 4 and 5).

[Test Example 3] Comparative Test of Methane-Production Inhibition with Existing Inhibitor BES (Comparative Compound)

In a glass vial (21.5 mL volume) for headspace analysis, 4.0 g of paddy field soil (provisional specific gravity 1.18 g/cm$^3$) was weighed, and 8 mL of distilled water was added. In this flooded soil, a plot to which 20 µL of acetone solution containing 100 ppm of Compound I-1 was added (0.5 mg/kg dry soil (equivalent to 590 g/ha)) is provided as Example 10, a plot to which 20 µL of an aqueous solution containing 100 ppm of BES (a comparative compound) and acetone was added (0.5 mg/kg dry soil) is provided as Comparative Example 3, and an untreated plot to which 20 µL of acetone was added is provided as Comparative Example 4. After 100 µL of a culture solution of paddy field soil microorganisms was added to these glass vials, the vials were tightly sealed using septum and aluminum caps, and allowed to stand at 30° C. for static incubation. After 21 and 28 days of incubation treatment, 0.5 mL of gas was collected from a headspace in a glass vial sample using a gas tight syringe and analyzed for methane production by gas chromatography (GC). The results are shown in Table 3. The comparative compound, BES (CAS No.: 4263-52-9; 2-Bromoethanesulfonate), is an existing methane-production inhibitor and a product manufactured by Tokyo Chemical Industry Co., Ltd.

TABLE 3

| | Compound | Treatment amount (mg/kg dry soil) | Methane-production amount (mg/L) 21 days after treatment | Methane-production amount (mg/L) 28 days after treatment |
|---|---|---|---|---|
| Example 10 | Compound I-1 | 0.5 | 13.4 | 34.2 |
| Comparative Example 3 | Comparative compound | 0.5 | 32.9 | 80.5 |
| Comparative Example 4 | Untreated | — | 69.3 | 119.2 |

In Test Example 3, the methane-production amount was reduced in both the Compound I-1 treated plot (Example 10) and the comparative compound treated plot (Comparative Example 3) compared to the untreated plot (Comparative Example 4), and the methane reduction amount due to Compound I-1 was significantly greater than the reduction amount due to the comparative compound.

The invention claimed is:

1. A method for inhibiting methane production, the method comprising applying a methane-production inhibitor composition to a water system or soil in which methane is generated, thereby inhibiting methane production from the water system or soil,
   wherein the methane-production inhibitor composition comprises one or more compounds selected from compounds represented by formula [I] as an effective ingredient:

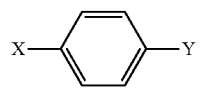
[I]

wherein X represents an —$OR_1$ group, a hydroxyl group, or a halogen atom, Y represents an —$OR_2$ group or an —$SO_2R_3$ group, $R_1$ represents a benzoyl group, $R_2$ represents a methylsulfonyl group or a chloromethylsulfonyl group, and $R_3$ represents a chloromethyl group or a hydroxymethyl group, and
   wherein the amount of methane-production inhibitor composition applied is an amount in the range of from 50 to 5,000,000 g of the compound represented by formula [I] per 1 ha of area of the water system or soil in which methane is generated.

2. The method for inhibiting methane production according to claim 1, wherein the water system in which methane is generated is a paddy field or a lake or marsh.

3. The method for inhibiting methane production according to claim 1, wherein the soil in which methane is generated is peatland.

4. A method for inhibiting methane production, the method comprising mixing a methane-production inhibitor composition with feed to form a mixture, and feeding the mixture to livestock, thereby inhibiting methane production from livestock breath and excreta,
   wherein the methane-production inhibitor composition comprises one or more compounds selected from compounds represented by formula [I] as an effective ingredient:

[I]

wherein X represents an —$OR_1$ group, a hydroxyl group, or a halogen atom, Y represents an —$OR_2$ group or an —$SO_2R_3$ group, $R_1$ represents a benzoyl group, $R_2$ represents a methylsulfonyl group or a chloromethylsulfonyl group, and $R_3$ represents a chloromethyl group or a hydroxymethyl group.

5. The method for inhibiting methane production according to claim 4, wherein the amount of methane-production inhibitor composition used is an amount in the range of from 0.05 to 5,000 mg of the compound represented by formula [I] per 1 kg of the feed.

6. A method for inhibiting methane production, the method comprising mixing a methane-production inhibitor composition with a compost or leaf mold material to ferment the compost or leaf mold material, thereby inhibiting methane production from a fermentation process of compost or leaf mold and from fully ripe compost or fully ripe leaf mold,
   wherein the methane-production inhibitor composition comprises one or more compounds selected from compounds represented by formula [I] as an effective ingredient:

[I]

wherein X represents an —$OR_1$ group, a hydroxyl group, or a halogen atom, Y represents an —$OR_2$ group or an —$SO_2R_3$ group, $R_1$ represents a benzoyl group, $R_2$ represents a methylsulfonyl group or a chloromethylsulfonyl group, and $R_3$ represents a chloromethyl group or a hydroxymethyl group.

7. The method for inhibiting methane production according to claim 6, wherein the amount of the methane-production inhibitor composition used is an amount in the range of from 0.05 to 5,000 mg of the compound represented by formula [I] per 1 kg of the compost or leaf mold material.

8. The method for inhibiting methane production according to claim 1, wherein the compound represented by formula [I] is any one of compounds represented by formulas [I-1] to [I-6]:

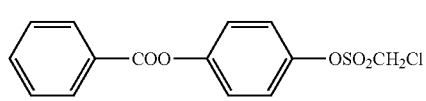
[I-1]

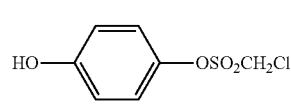
[I-2]

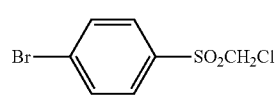
[I-3]

-continued

[I-4]
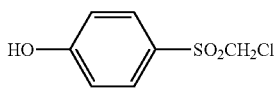

[I-5]
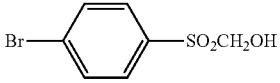

[I-6]
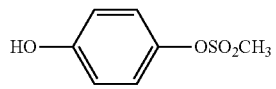

9. The method for inhibiting methane production according to claim 4, wherein the compound represented by formula [I] is any one of compounds represented by formulas [I-1] to [I-6]:

[I-1]
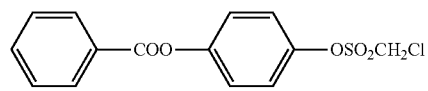

[I-2]
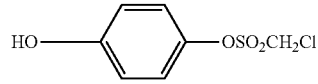

[I-3]
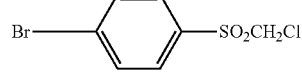

[I-4]
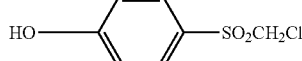

[I-5]
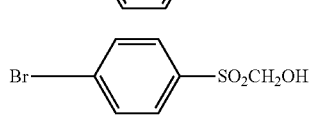

-continued

[I-6]
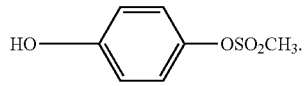

10. The method for inhibiting methane production according to claim 6, wherein the compound represented by formula [I] is any one of compounds represented by formulas [I-1] to [I-6]:

[I-1]
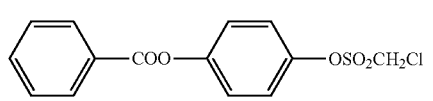

[I-2]
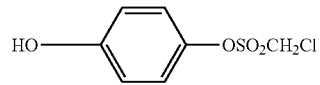

[I-3]
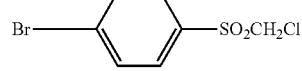

[I-4]
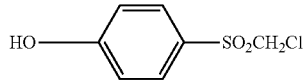

[I-5]
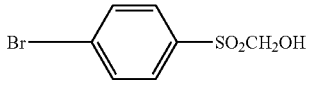

[I-6]
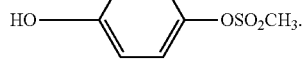

* * * * *